(12) United States Patent
Letellier

(10) Patent No.: US 9,259,345 B2
(45) Date of Patent: Feb. 16, 2016

(54) CATHETER BAG AND HARNESS

(71) Applicant: Godfrey T. Letellier, Toronto (CA)

(72) Inventor: Godfrey T. Letellier, Toronto (CA)

(*) Notice: Subject to any disclaimer, the term of this patent is extended or adjusted under 35 U.S.C. 154(b) by 0 days.

(21) Appl. No.: 13/786,537

(22) Filed: Mar. 6, 2013

(65) Prior Publication Data

US 2013/0245585 A1     Sep. 19, 2013

(30) Foreign Application Priority Data

Mar. 6, 2012   (CA) ..................................... 2770007

(51) Int. Cl.
*A61F 5/44*     (2006.01)
*A61F 5/445*    (2006.01)
(Continued)

(52) U.S. Cl.
CPC ................. *A61F 5/4408* (2013.01); *A61F 5/44* (2013.01); *A61F 5/4404* (2013.01); *A61F 5/445* (2013.01); *A61J 1/10* (2013.01); *A61J 1/12* (2013.01); *A61J 1/14* (2013.01); *A41F 9/002* (2013.01); *A45C 13/30* (2013.01); *A45F 3/02* (2013.01);
(Continued)

(58) Field of Classification Search
CPC ....... A45F 3/02; A45F 3/12; A45F 2003/148; A45F 2004/006; A45F 2200/0575; A45F 2005/006; A45F 2005/008; A45F 5/02; A45F 5/021; A45F 2003/002; A45F 3/005; A45F 2003/006; A45F 2003/007; A45F 2003/008; A45F 2003/025; A45F 3/14; A45F 2003/142; A45F 2003/144; A45F 2003/146; A45F 5/4408; A45F 5/453; A45F 5/455; A45F 5/44; A45F 5/4404; A01D 46/22; A01D 46/24; A01D 46/243; A61F 5/4408; A63B 21/065; A61M 39/14; A61M 39/18; A61M 2039/1027; A45C 13/30; A45C 9/00; A61J 1/10; A61J 1/12; A61J 1/14; A41F 9/002; A41F 9/005; A41F 9/007; Y10S 2/912; Y10S 2/92; G09F 3/005; G09F 2003/023; G09F 2003/0251; G09F 2003/0254; G09F 2003/0272; G09F 3/10
USPC .......... 604/328, 343, 345; 224/660, 661, 662, 224/257, 625, 626, 637, 638, 639, 677
See application file for complete search history.

(56) References Cited

U.S. PATENT DOCUMENTS 1,292,728 A * 1/1919 Dozier ........................... 224/625
3,601,125 A * 8/1971 Moss ............................. 604/347
(Continued)

FOREIGN PATENT DOCUMENTS

WO      WO 92/03994      * 3/1992  ................ A61F 5/44

OTHER PUBLICATIONS

Blog on "Urine Bag Holders" featured on http://www.thewheelchairsite.com/urine-bag-holders.aspx.
(Continued)

*Primary Examiner* — Adam Marcetich
(74) *Attorney, Agent, or Firm* — Tyson B. Benson; Advent, LLP

(57) ABSTRACT

The disclosure includes embodiments of an improved catheter bag comprising a bag portion, a top tab portion and a bottom tab portion with a one way entry valve extending through said top tab portion to permit fluid to enter the bag portion. A draining valve is provided in the bottom tab portion operable from an open to a closed position. The catheter bag is provided with pairs of parallel vertical slots sized and shaped to retain straps for retaining the bag against the body.

4 Claims, 4 Drawing Sheets

(51) Int. Cl.
  *A61J 1/10* (2006.01)
  *A61J 1/12* (2006.01)
  *A61J 1/14* (2006.01)
  *A45C 13/30* (2006.01)
  *A41F 9/00* (2006.01)
  *A45F 3/02* (2006.01)
  *A45F 5/00* (2006.01)
  *A45F 3/14* (2006.01)
  *A45F 5/02* (2006.01)

(52) U.S. Cl.
  CPC .. *A45F 3/14* (2013.01); *A45F 5/021* (2013.01); *A45F 2003/144* (2013.01); *A45F 2005/008* (2013.01)

(56) References Cited

U.S. PATENT DOCUMENTS

| | | | | |
|---|---|---|---|---|
| 3,897,785 A * | 8/1975 | Barto, Jr. | | 604/327 |
| 4,073,295 A * | 2/1978 | Laufbahn | | 604/353 |
| 4,187,846 A * | 2/1980 | Lolachi et al. | | 604/411 |
| 4,319,573 A * | 3/1982 | Whitlock | | 604/328 |
| 4,511,358 A * | 4/1985 | Johnson et al. | | 604/327 |
| 4,634,437 A * | 1/1987 | Lowthian | | 604/323 |
| 4,723,944 A * | 2/1988 | Jensen | | 604/323 |
| 4,846,816 A * | 7/1989 | Manfredi | | 604/323 |
| 4,870,961 A * | 10/1989 | Barnard | | 128/202.27 |
| 4,909,478 A * | 3/1990 | Steer | | 251/352 |
| 4,938,747 A * | 7/1990 | Wallace | | A61F 5/44 604/317 |
| 4,944,043 A * | 7/1990 | Bush | | 2/308 |
| 4,955,879 A * | 9/1990 | Mervine | | 604/327 |
| 5,002,541 A * | 3/1991 | Conkling et al. | | 604/319 |
| 5,053,027 A * | 10/1991 | Manfredi | | 604/327 |
| 5,084,037 A * | 1/1992 | Barnett | | 604/349 |
| 5,231,420 A * | 7/1993 | Yamamoto et al. | | 347/200 |
| 5,405,336 A * | 4/1995 | Austin et al. | | 604/534 |
| 5,667,877 A * | 9/1997 | Tajiri et al. | | 428/195.1 |
| 5,718,364 A * | 2/1998 | McDowell | | 224/603 |
| 5,807,299 A * | 9/1998 | McRoberts et al. | | 602/67 |
| 6,065,154 A * | 5/2000 | Hulings et al. | | 2/102 |
| 6,129,709 A * | 10/2000 | Millen | | 604/179 |
| 6,149,042 A * | 11/2000 | Rassias | | 224/661 |
| 6,296,627 B1 * | 10/2001 | Edwards | | 604/347 |
| 6,887,223 B2 * | 5/2005 | Bisbee | | 604/353 |
| 7,993,313 B1 * | 8/2011 | Roche | | 604/345 |
| 8,177,765 B2 * | 5/2012 | House | | 604/317 |
| 8,361,044 B2 * | 1/2013 | Marshall | | 604/327 |
| 8,608,718 B1 * | 12/2013 | Patterson-Young | A61F 5/4408 | 604/345 |
| 2003/0121945 A1 * | 7/2003 | Lemanski, II | | 224/579 |
| 2005/0159779 A1 * | 7/2005 | Schwartz et al. | | 606/234 |
| 2006/0142730 A1 * | 6/2006 | Proulx et al. | | 604/403 |
| 2006/0293631 A1 * | 12/2006 | Bolt | A61F 5/449 | 604/353 |
| 2007/0260208 A1 * | 11/2007 | May | | 604/345 |
| 2008/0185412 A1 * | 8/2008 | Hollins | | 224/661 |
| 2010/0007134 A1 * | 1/2010 | Elton et al. | | 285/31 |
| 2010/0152686 A1 * | 6/2010 | Ryder et al. | | 604/332 |
| 2010/0294821 A1 * | 11/2010 | Szabo | | 224/661 |
| 2011/0172491 A1 * | 7/2011 | Piskun et al. | | 600/104 |
| 2011/0202024 A1 | 8/2011 | Cozzens | | |
| 2012/0006867 A1 * | 1/2012 | Caldwell | | 224/191 |

OTHER PUBLICATIONS

Product information available for review and purchase on ht p:// www.allegromedical.com/catheters-c539/carefix-leg-bag-holder-p559805.html.
Advertisement and information featured on http://catheze.com/.

* cited by examiner

CATHETER BAG AND HARNESS

FIELD OF THE INVENTION

The present invention relates generally to a harness for attachment to a catheter bag to maintain the catheter bag in a stable and more comfortable position.

BACKGROUND OF THE INVENTION

When using a catheter, a collection bag for the urine is often placed along the leg of the patient. Numerous different types of devices have been developed to hold the urine or catheter bag. In most cases if the patient is mobile and active (walking) over time the bag has a tendency to slip down the leg putting stress on the catheter hose that is connected to the patient's bladder.

In addition when sleeping, if the patient is tossing and turning or moving around in their sleep, strain is again placed on the catheter hose. The bag often begins to rotate on the leg and ends up either around to the other side of the leg or works its way down the leg again, putting pressure on the catheter hose.

Another problem with many known catheter bags is the catheter bag will have a tendency to bunch up and when this happens it creates an area of chafing and discomfort for the wearer. The bag is long and in cases the bag is positioned close to the knee joint and as the bag slips slightly when sitting or moving around the edges of the bag catch the area where the knee bends, giving the wearer another chafing area.

There is a need for a better system of holding the catheter or urine bag on the leg of the patient so that it does not slip down the leg. There is also a need for improvements I the design of the catheter bags to provide better comfort to the patient.

SUMMARY OF THE INVENTION

One embodiment of the present invention provides a harness for holding a catheter or urine bag against a patient's leg, the harness comprising a lower leg strap portion, an upper leg strap portion and a shoulder strap portion.

The lower leg strap portion is sized and shaped to feed through a pair of slots near a bottom edge of a catheter bag and go around a patient's leg.

The upper leg strap portion is sized and shaped to feed through a pair of slots near a top edge of a catheter bag and go around a patient's leg.

The shoulder strap portion is sized and shaped to have one end connect to one side of upper leg strap portion go over the patient's shoulder and the other end connect to another side of upper leg strap portion.

The shoulder strap portion has an means to adjust the length of the shoulder strap portion when in use to adjust the vertical positioning of the catheter bag on the patient's leg.

In another embodiment the present invention provides an improved catheter bag comprising a bag portion a top tab portion and a bottom tab portion with a one way entry valve extending through said top tab portion to permit fluid to enter the bag portion, a draining valve in the bottom tab portion operable from an open to a closed position. The catheter bag is provided with a first pair of parallel vertical slots sized and shaped to retain an upper leg strap located below a top edge of the catheter bag within the top tab portion with one of said first pair of slots is located on one side of the one way entry valve and the other of said first pair of slots located on the other side of the one way entry valve and spaced apart but close enough to avoid bunching of the top tab portion when in use. A second pair of parallel vertical slots, sized and shaped to retain a lower leg strap, are located above a bottom edge within the bottom tab portion and with one of said second pair of slots located on one side of the draining valve and the other of said second pair of slots located on the other side of the draining valve and spaced apart but close enough to avoid bunching of bottom tab portion when in use.

The draining valve is preferably a push-pull valve.

Two "O" rings may be placed on a stem of the one way entry valve to which a catheter hose is connected to reduce the risk of the hose disengaging from the entry valve.

The corners of the upper and lower tab portions may be rounded.

Further features of the invention will be described or will become apparent in the course of the following detailed description.

BRIEF DESCRIPTION OF THE DRAWINGS

In drawings which illustrate by way of example only one embodiment of the invention.

Similar references are used in different figures to denote similar components.

DETAILED DESCRIPTION OF THE PREFERRED EMBODIMENTS

Figure 1:
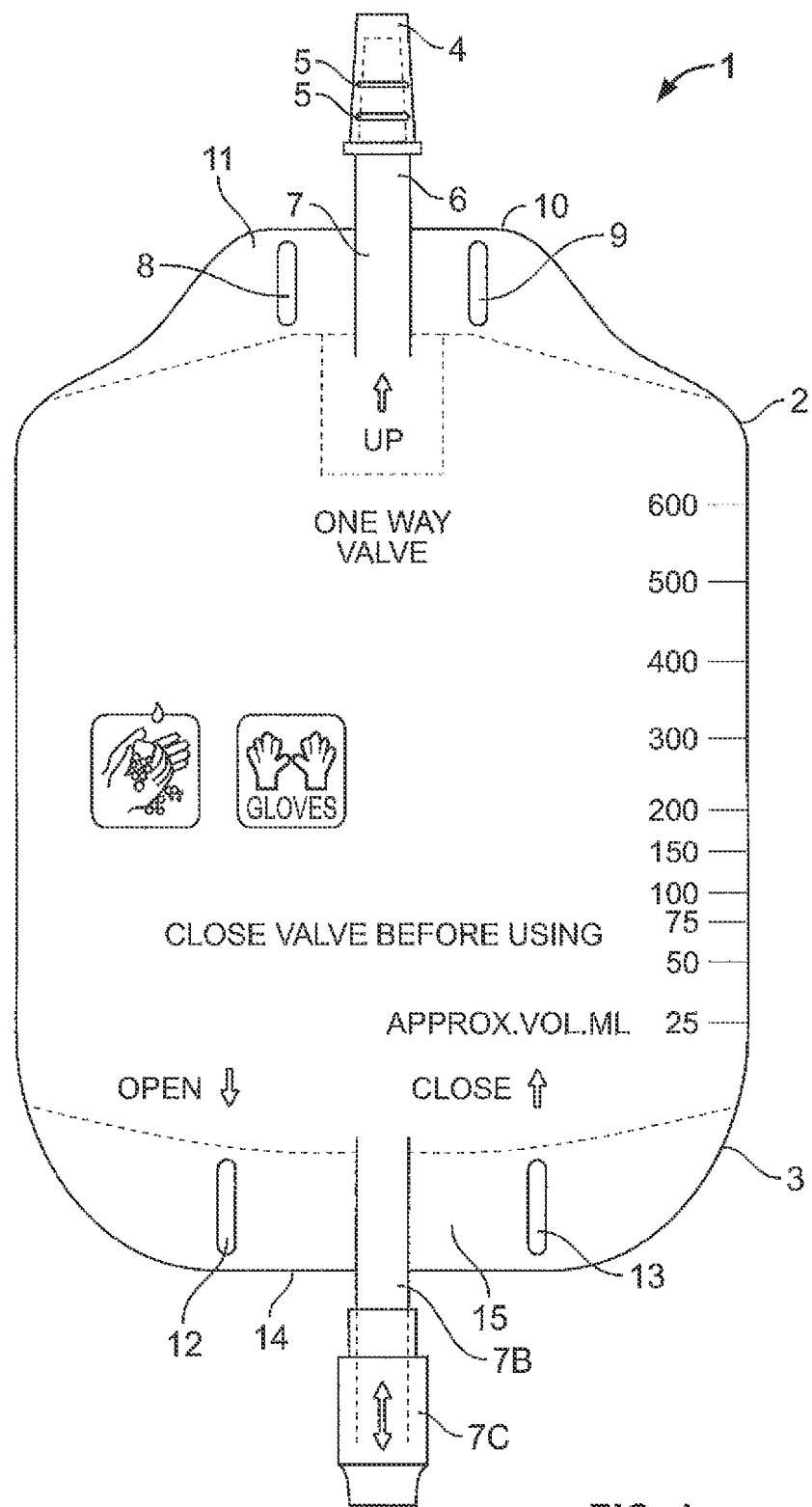
FIG. 1 illustrates one embodiment of an improved design for a catheter bag in accordance with the present invention.

Referring now to the figures in detail FIG. 1 illustrates one embodiment of an improved design of a catheter or urine bag, generally indicated at 1, in accordance with the present invention.

Known catheter or urine bags have a draining valve at the bottom of the bag. For security reasons the valve may be a twist valve that requires two hands to twist open. This may pose problems for some patients who are disabled or only have one arm or hand or suffer from arthritis. The prior art valves if not fully closed may open up at some of the most inconvenient times. Accordingly in the embodiment illustrated the draining valve 7B shown in FIG. 1 is a push-pull valve 7C. Push to close and pull to open. Instead of a turning motion that requires two hands the valve 7B is a push pull valve. This valve can be used easily by all, as you need only one hand to open the valve and to close the valve and all you have to do is bend the valve away from the leg and push it closed, making it easier to close. The valve cannot be opened by a twisting motion by the patient while he or she is moving.

Conventional catheter bag designs feature an entry valve at the top of the bag to which a hose from the patient's bladder is attached. As the patient moves around the strain on the hose may cause it to detach from the catheter bag. In the design according to the present invention illustrated in FIG. 1, where the hose 4 meets the catheter bag 1, two "O" rings 5 have been placed on the stem 6 of one way entry valve 7 to reduce the risk of the hose 4 from disengaging from the valve 7 on catheter bag 1.

The corners of known catheter or urine bags are typically square and thereby can be a little sharp creating chafing and discomfort. In the design of the catheter bag 1 shown in FIG. 1 the upper 2 and lower 3 corners of the bag 1 have been rounded to help avoid problems encountered with known designs. In addition the design of the catheter bag 1 shown in FIG. 1 is shorter than known bags so that the bag doesn't interfere with the knee joint and the risk of chafing is reduced. The bag 1 shown in FIG. 1 is also wider than known bags, to give the bag 1 a similar volume of liquid that can be retained. In the embodiment illustrated intended for use with adult patients bag 1 is about 20 cm long and about 14 cm wide when empty of fluid. The presented invention is not restricted to bags having these dimensions and bags having different sizes can be provided according to the present invention.

Figure 2:
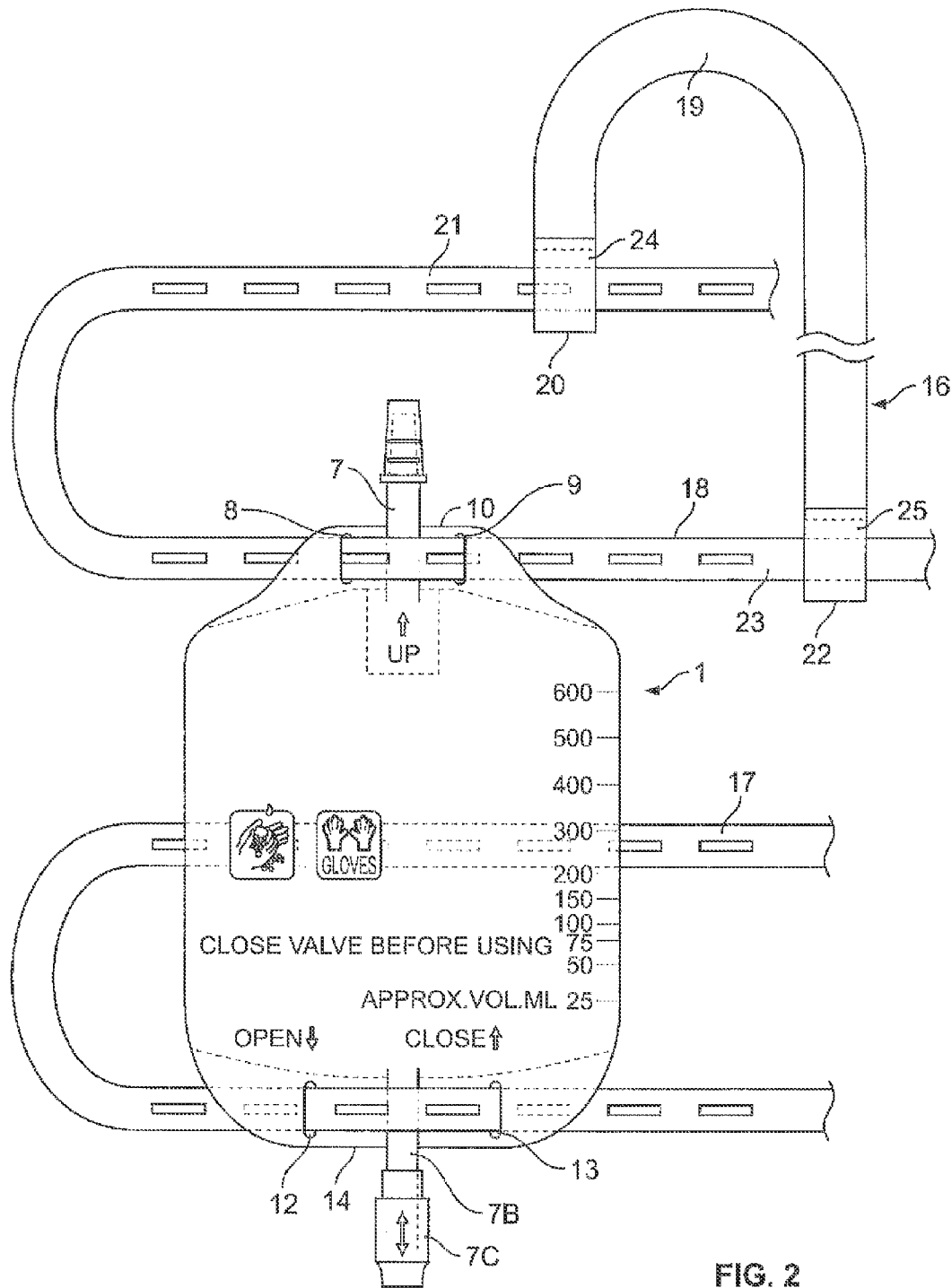
FIG. 2 illustrates the catheter bag of FIG. 1 in combination with one embodiment of a harness (schematically shown) in accordance with the present invention for maintaining the catheter bag in position.

In order to work with the embodiment of the harness shown in FIG. 2, catheter bag 1 is provided with a pair of parallel vertical slots 8,9 sized and shaped to retain an upper leg strap of the harness according to the present invention shown in FIG. 2. Slots 8,9 are located below the top edge 10 of bag 1. The top edge 10 is preferably part of a top tab portion 11 of bag 1 that is not designed to retain any fluid. In the embodiment illustrated one of said slots 8 is located on one side of one way entry valve 7 and the other of said slots 9 is located on the other side of valve 7. The slots 8, 9 are spaced apart but close enough to avoid bunching of tab portion 11 when in use.

In the embodiment illustrated in FIG. 1, catheter bag 1 is further provided with a pair of parallel vertical slots 12,13 sized and shaped to retain a lower leg strap of the harness according to the present invention shown in FIG. 2. Slots 12,13 are located above the bottom edge 14 of bag 1. The bottom edge 14 is preferably part of a bottom tab portion 15 of bag 1 that is not designed to retain any fluid. In the embodiment illustrated one of said slots 12 is located on one side of draining valve 7B and the other of said slots 13 is located on the other side of valve 7B. The slots 12, 13 are spaced apart but close enough to avoid bunching of tab portion 15 when in use.

Figure 3:
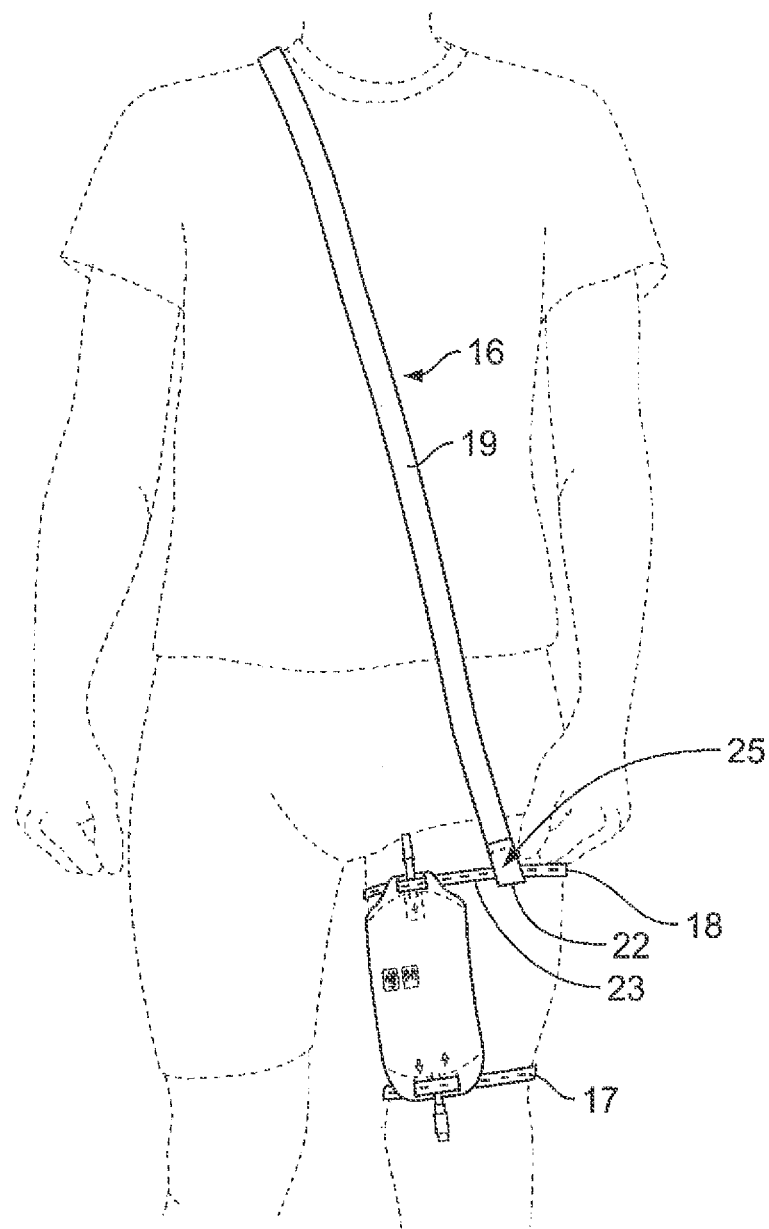
FIG. 3 shows a front view of the catheter bag and harness of FIG. 2 as worn by an individual.
Figure 4:
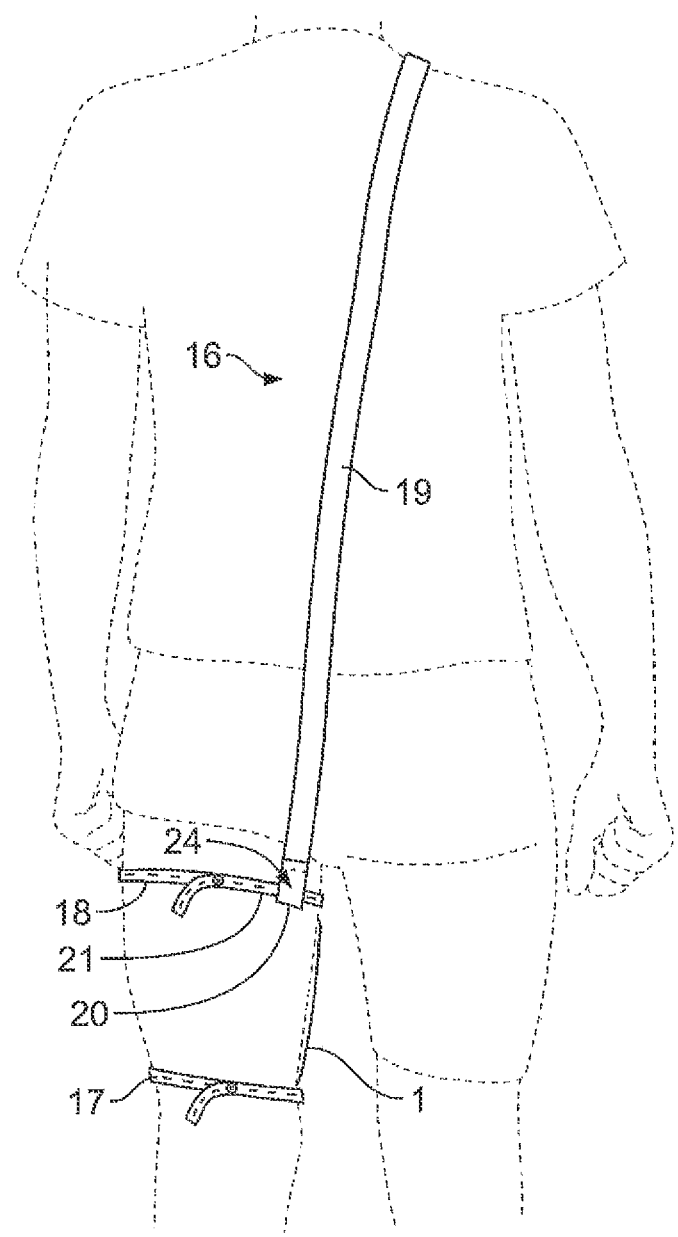
FIG. 4 shows the back view of the individual shown in FIG. 3 wearing the catheter bag and harness of FIG. 2.

Referring to FIGS. 2 to 4, one embodiment of a harness according to the present invention, generally indicated at 16, is schematically illustrated in combination with catheter bag 1. Harness 16 comprises a lower leg strap portion 17, an upper leg strap portion 18 and a shoulder strap portion 19.

Lower leg strap portion 17 is sized and shaped to feed through slots 12,13 near the bottom edge 14 of catheter bag 1 and go around the patient's leg. Lower leg strap portion 17 can be made from an elastic material to adapt to different leg sizes or can be provided with a connection at each end to permit the length of the strap 17 when in use to be adjusted.

Upper leg strap portion 18 is sized and shaped to feed through slots 8,9 near the bottom edge 10 of catheter bag and go around the patient's leg. Upper leg strap portion 18 can be made from an elastic material to adapt to different leg sizes or can be provided with a connection at each end to permit the length of the strap 18 when in use to be adjusted.

When the straps 17,18 are attached the straps 17,18 go under the bag 1 to the slots 12,13 or 8,9 up into the slots 12 or 8 over the valves 7 or 7B and down through the other slot 13 or 9 respectively for the lower leg strap portion 17 and upper leg strap portion 18. This improvement makes the bag 1 sit firmly against the patient's leg. Bunching of the bag 1 is greatly reduced or eliminated. The bag valves 7 and 7B sit flat on the patient's leg.

Shoulder strap portion 19 is sized and shaped to have one end 20 connect to one side 21 of upper leg strap portion 18 and the other end 22 connect to the other side 23 of upper leg strap portion 18. The upper leg strap portion 18 encircles the leg front and back. Without the harness, even if the patient over tightens the straps 17, 18 the bag 1 still has a tendency to move down the leg. The straps 17,18 also pinch the leg.

Shoulder strap portion 19 is intended to go over the shoulder of the patient, left or right (for catheter bag placed against left leg the shoulder strap 19 goes over the right shoulder and vice versa). In the embodiment illustrated the shoulder strap 19 is about 3 cm wide and the thickness is ¼ mm clear pliable plastic which is 1.8 m to 2 m in length.

The shoulder strap portion 19 has an area 24 at the one end 20 that is made to go over the shoulder and down the back of the patient and then attached to the rear side 21 upper leg strap 18. The area 24, about 6" long in the embodiment illustrated has a sticky surface. The patient peels off the protective cover (not shown) over area 24 and takes the sticky area which goes under the strap 18 and folds it over the strap 18 to the required line on the shoulder strap portion 19.

The other end 22 of shoulder strap portion 19 is intended to go over the patient's shoulder, down the chest and then attached to the front side 23 upper leg strap 18. The other end 22 has an area 25 that is also sticky with a pressure sensitive release backing paper. The patient peels off the protective cover (not shown) over area 25 and takes the sticky area which goes under the strap 18 and folds it over the strap 18 to position the bag 1 at the most comfortable position on the leg. The patient leaves a little slack in shoulder strap 19 for movement while the patient is moving. This makes it comfortable for the wearer.

This new and improved catheter bag and harness reduces the strain on the catheter hose, reduces the risk of the catheter bag slipping down the leg and reducing the risk of chafing. The patient is able to run, jog, walk, do chores and even ride a bicycle. Life improves immensely with the harness of the present invention by holding the catheter bag in place with no or very little movement of the bag.

It is to be understood by one of ordinary skill in the art that the present discussion is a description of exemplary embodiments only, and is not intended to limit the broader aspects of the present invention.

Although various preferred embodiments of the present invention have been described herein in detail, it will be appreciated by those skilled in the art, that variations may be made thereto without departing from the spirit of the invention or the scope of the appended claims.

The embodiments of the invention in which an exclusive property or privilege is claimed are defined as follows:

1. An improved catheter bag comprising:
    a bag portion, a non-fluid retaining top tab portion, and a non-fluid retaining bottom tab portion with a one way entry valve extending through said top tab portion to permit fluid to enter the bag portion, a draining valve in the non-fluid retaining bottom tab portion operable from an open to a closed position, the draining valve defining an outer surface for engaging an inner surface of a push-pull valve,
    two "O" rings disposed about a stem of the one way entry valve to which a catheter hose is configured to connect to reduce risk of the catheter hose disengaging from the entry valve,
    wherein the catheter bag is provided with a first pair of parallel vertical slots sized and shaped to retain the stem between an upper leg strap and the non-fluid retaining top tab portion with the upper leg strap located below a top edge of the catheter bag within the non-fluid retaining top tab portion with one of said first pair of slots is located on one side of the one way entry valve and the other of said first pair of slots located on the other side of the one way entry valve and spaced apart, and a second pair of parallel vertical slots sized and shaped to retain a lower leg strap, the upper leg strap configured to connect with a shoulder strap portion, said second pair of vertical slots located above a bottom edge within the bottom tab portion and with one of said second pair of slots located on one side of the draining valve and the other of said second pair of slots located on the other side of the draining valve and spaced apart.

2. The catheter bag of claim 1 wherein corners of the upper and lower tab portions are rounded.

3. A catheter bag assembly comprising:
   a lower leg strap portion;
   an upper leg strap portion;
   a shoulder strap portion coupled to the upper leg portion; and
   a bag portion, a non-fluid retaining top tab portion, and a non-fluid retaining bottom tab portion with a one way entry valve extending through the top tab portion to permit fluid to enter the bag portion, a draining valve in the non-fluid retaining bottom tab portion operable from an open to a closed position, the draining valve defining an outer surface for engaging an inner surface of a push-pull valve,
   wherein the catheter bag is provided with a first pair of parallel vertical slots sized and shaped to retain a stem between the upper leg strap portion and the non-fluid retaining top tab portion with the upper leg strap disposed below a top edge of the catheter bag within the non-fluid retaining top tab portion with one of the first pair of slots is disposed on one side of the one way entry valve and the other of the first pair of slots disposed on the other side of the one way entry valve and spaced apart, and a second pair of parallel vertical slots sized and shaped to retain the lower leg strap portion, the second pair of vertical slots disposed above a bottom edge within the non-fluid retaining bottom tab portion and with one of the second pair of slots disposed on one side of the draining valve and the other of the second pair of slots disposed on the other side of the draining valve and spaced apart.

4. The catheter bag assembly as recited in claim 3, further comprising at least one "O" ring disposed about a stem of the one way entry valve to which a catheter hose is connected to reduce the risk of the hose disengaging from the entry valve.

\* \* \* \* \*